United States Patent [19]

Berg

[11] 3,960,901

[45] June 1, 1976

[54] PREPARATION OF CITRACONIC ACID

[75] Inventor: Rudolph G. Berg, Groton, Conn.

[73] Assignee: Pfizer Inc., New York, N.Y.

[22] Filed: Apr. 7, 1975

[21] Appl. No.: 565,432

Related U.S. Application Data

[63] Continuation-in-part of Ser. No. 396,872, Sept. 12, 1973, abandoned.

[52] U.S. Cl. ..................... 260/346.8 R;- 260/537 N
[51] Int. Cl.² ................. C07D 307/60; C07C 51/00
[58] Field of Search ...................... 260/346.8, 537 N

[56] References Cited

UNITED STATES PATENTS 3,835,162    9/1974    Tate et al. .................... 260/346.8

*Primary Examiner*—Harry I. Moatz
*Attorney, Agent, or Firm*—Connolly and Hutz

[57] ABSTRACT

High purity citraconic acid is prepared in good yield by the thermolysis, in the presence of a catalyst, of citramalic acid, 3-methylmalic acid, paraconic acid, mesaconic acid and mixtures thereof.

10 Claims, No Drawings

PREPARATION OF CITRACONIC ACID

CROSS-REFERENCE TO RELATED APPLICATIONS

This application is a continuation-in-part of application Ser. No. 396,872, filed Sept. 12, 1973, now abandoned,

BACKGROUND OF THE INVENTION

Citraconic anhydride is a useful intermediate for the curing of epoxy resins.

U.S. Pat. NO. 2,966,498 describes a method for the production of citraconic anhydride by heating itaconic acid in the presence of an alkali metal dihydrogen phosphate or sulfate at elevated tempertures.

The preparation of citraconic acid by the vapor phase catalytic dehydration and decarboxylation of related six-carbon acids such as citric acid, isocitric acid, aconitic acid and mixtures thereof is described in U.S. Pat. No. 3,701,805.

In a process reported by Kunichika, S., Oka, S., Tanaki, H., in Bull. Inst. Chem. Res., Kyoto University 44, No. 3, 221–225 (1966), citraconic acid was prepared by the pyrolysis of the acetate of the anhydride of citramalic acid.

SUMMARY OF THE INVENTION

This invention is concerned with a process for the preparation of citraconic acid or anhydride which comprises heating at short exposure time in an inert atmoshpere at a temperature of 160°–330°C. citramalic acid, mesaconic acid, paraconic acid, 3-methylmalic acid or mixtures thereof in the presence of an alkali or alkaline earth salt of phosphoric acid, removing continuously formed gaseous product from the reaction zone and recovering said product as citraconic acid or anhydride.

DETAILED DESCRIPTION OF THE INVENTION

Thermolysis of citramalic acid, 3-methylmalic acid, paraconic acid, mesaconic acid and mixtures thereof under the conditions of this invention gives citraconic acid in good purity and yield. The direct product of the process is citraconic anhydride which may be partly or completely hydrolyzed to the acid according to the method of recovery. The catalysis and the elevated temperatures of the process are such that the reactions are believed to proceed through anhydrides or lactides of the starting acids. Such materials may be considered equivalents of the acid forms for this process.

The inter-relationship of several five-carbon dicarboxylic acids is outlined as follows:

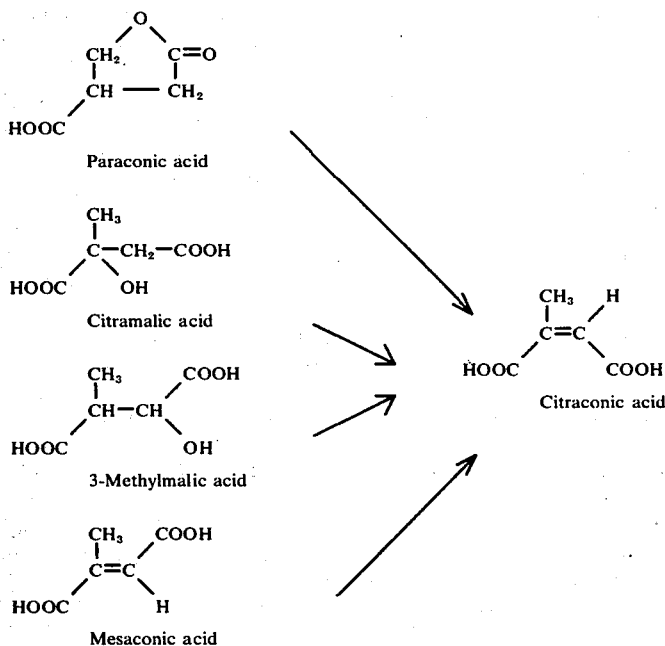

Citramalic acid is available through its preparation from ethyl acetoacetate and potassium cyanide, Biochemical Preparations 9, 26 (1962), John Wiley & Sons Inc., New York. Paraconic acid may be prepared by the method reported by Fittig and Beer, Annalen 216, 79–90. 3-Methylmalic acid can be prepared by the method described in J. Am. Chem. Soc. 68, 912–13 (1946). The preparation of mesaconic acid is described in Org. Syn. 11, 74 (1931).

Reference is made in the Dictionary of Organic Compounds, 4th Edition, pages 714, 2092, 2993 (1965), New York, Oxford University Press, to the fact that mesaconic acid has a melting point of 240.5°C., a temperature that falls in the temperature range of the process of the present invention. However, there are no prior reports that mesaconic acid is converted to citraconic acid at its melting point. However, it has been found during the course of these investigations that small amounts of citraconic anhydride are formed when the heating time is at least 3 minutes. When a catalyst is used, the amount and rates of citraconic anhydride formation are much greater. Thermal stabilities of the reactant and citraconic anhydride product are moderately good, but loss due to decomposition occurs if exposure to elevated temperatures is lengthy.

Removal of citraconic anhydride immediately upon formation is an integral part of the present invention. The methods of the present invention provide yields of citraconic acid or anhydride of up to 98% from mesaconic acid.

Reitter discloses in Berichte 31, 2724–25 (1898) the distillation of paraconic acid on an open flame to produce citraconic anhydride. The reported yield of citraconic anhydride was 73.5% (based on the collected monoanilide). However, there is no record of the temperature being controlled at 160°–300°C., the temperature range of the present invention process. Fittig in Annalen 255, 15 (1889) states the citraconic anhydride is the main product from the distillation of paraconic acid, but no quantitative data are presented. Data from the investigations of the process of the present invention show that distillation of paraconic acid with no catalyst gives a 79% yield of crude citraconic anhydride in contrast to a yield of 96% with a catalyzed procedure.

Michael and Tissot, J. Prakt. Chem., 46, 285, disclose the distillation of citramalic acid to give citraconic anhydride. No yields are given but evolution of carbon dioxide is mentioned indicating decomposition, probably to methacrylic acid, carbon dioxide and water. Under the conditions of the process of the present invention which minimize decomposition, the yield of citraconic anhydride from citramalic acid is raised from 53% without catalyst to 76% with catalyst.

The key features of the process of the present invention reside in the thermal conversion of citramalic acid, paraconic acid, 3-methylmalic acid, mesaconic acid and mixtures thereof under (a) controlled temperature conditions, (b) the use of selected catalysts and (c) limited exposure of reactants and of formed citraconic anhydride or acid to elevated temperatures. High yields of citraconic acid or anhydride of excellent purity are obtained.

In a preferred embodiment of this invention, a spray mist mixture containing inert diluent and reactant can be formed conveniently by passing an inert diluent gas through an aspirator to mix with a fine stream of a solution of reactant. While aqueous soltuions are convenient, inexpensive and safe, solutions in solvents such as lower ketones which include acetone, methyl ethyl ketone, methyl propyl ketone, methyl isobutyl ketone, etc. may also be used. This resulting spray mist mixture almost instantaneously becomes vaporized upon entering the reaction zone, a hot bed of solid, stable, particulate material. Not being critical, any gas which is inert to the reaction products or starting material, including substances such as nitrogen, helium, carbon dioxide, super-heated steam or recycled effluent gases after removal of the low volatility reaction products, can be employed for the diluent gas feed portion of the system. Also, the spray mist mixture may comprise an inert diluent gas containing the reactant finely dispersed therein as solution or liquid droplets, solid particles or mixtures thereof.

The reactor bed support material contains a catalyst deposited by coating or impregnation. The surface area of the support material is not critical but it has been found that satisfactory results are obtained where the surface area is about 10–50 square meters/gram.

The support material may be selected from a group of materials consisting of aluminum oxide, silicon carbide, zirconium silicate, zirconium oxide, silicon dioxide and a mixture of aluminum oxide and silicon dioxide. The preferred support material is aluminum oxide. These support materials are not considered to be catalysts within the scope of the present invention. However, some or all may have a certain degree of catalytic activity. It has been found that citraconic anhydride is produced from the described starting materials in unsatisfactory lesser amounts when catalyst has not been deposited on support materials. Whether this partial conversion to citraconic anhydride is purely thermal or partially catalyzed by the support material is not known.

The use of a catalyst for these reactions provides significant advantage over prior art. Yields are improved, the reaction ternperature is lowered and by-product formation is decreased. In addition, the optimum reaction temperatures for each of the five-carbon acids are brought into a narrower range which is particularly advantageous when processing mixtures of the acids.

Preferably, the concentration of active catalyst material is from about 0.01–20 weight percent, based on the total weight of support plus catalyst material; however, best results are obtained where the concentration is about 0.1–5 weight percent.

The active catalyst may be selected from any of the broad class of alkali and alkaline earth metal salts of phosphoric acid. The term "phosphoric acid" includes the common oxygen acids where phosphorus is in the +5 valence state. Included are orthophosphoric acid, pyrophosphoric acid, metaphosphoric acids and polyphosphoric acids. Typical active catalysts include potassium pyrophosphate, sodium pyrophosphate, calcium pyrophosphate, strontium pyrophosphate, rubidium phosphate, cesium phosphate, barium phosphate, calcium phosphate, sodium tripolyphosphate, potassium metaphosphate, etc.

The phosphate salts may be generated in situ. e.g. from potassium hydroxide and orthophosphoric acid, from sodium citramalate and phosphoric acid, etc. The preferred compound is potassium dihydrogen phosphate. In the presence of the organic acids, it is presumed that all of the operable catalysts in use exist as the metal hydrogen phosphates.

Although the shape of the reactor is not critical, the reaction is conveniently carried out in a tubular reactor packed with the catalyst and support. In this case, the catalyst bed diameter to length ratio can be from about 4:1 to 1:100, and is preferably about 1:4.

Very brief contact times between both gaseous reactants and citraconic anhydride and the reaction bed are desired to prevent undesired side-products and residue from forming which would limit the useful life of the bed and give reduced yields of citraconic acid and/or anhydride. The contact time is, of course, dependent on the reaction temperature at which the thermolysis is carried out. Contact times may be about 5 seconds at 220°–280°C. to about 0.01 second at 300°–330°C., calculated as the ratio of bed void volume to rate of gas flow through the bed. Preferably, contact times and temperatures are 0.2–1 second at 220°–280°C.

The desired citraconic acid/anhydride product in the gaseous effluent from the reactor can be typically recovered by condensation in a series of cold traps, absorption in a scrubber using water or some other suitable absorption liquid or by fractional distillation procedures. Actual isolation of citraconic acid/anhydride from aqueous mixtures can be accomplished by the usual techniques including azeotroptic drying to the anhydride followed by distillation. The crude aqueous product as obtained, however, is usually clean enough to be employed in many applications without further purification.

The desired thermolytic conversion of citramalic acid, 3-methylmalic acid, paraconic acid, mesaconic acid or mixtures of these acids to citraconic acid or anhydride may also be carried out by distillative processes. The reactants are introduced into a distillation vessel and brought to the reaction temperature of 190°–250°C., and under a pressure of 5 mm Hg to slightly above atmospheric pressure, preferably 15–100 mm Hg, while distilling and collecting the product as citraconic anhydride, acid or mixtures thereof. Times of exposure of reactants and products to elevated temperatures is desirably limited to less than 30 minutes and preferably to less than 10 minutes. Use of the metal phosphates previously described as catalysts at a level of 0.01–5 weight percent, preferably 0.1–2.5%, based on average weight of reaction mixture in the vessel, over the course of the thermolysis allows reaction to occur at a lower temperature, thereby decreasing the extent of by-product formation. Use of a catalyst is critical to operation of the invention in order to obtain the desired high yields of citraconic anhydride or acid. In reactions involving mixtures of the acids, it also brings the optimum temperature for conversion of each acid into the same temperature range. While the five-carbon acids or mixtures thereof may be charged all at once as solids or solutions, it is especially desirable to introduce the acids continuously as aqueous solutions while citraconic anhydride is formed and removed continously.

The following examples are provided for illustrative purposes and should not be interpreted as limiting the invention the scope of which is defined by the appended claims.

EXAMPLE I

An Alundum support (aluminum oxide) such as Norton Products No. LA3032m ⅛ × ⅛ inch pellets was extracted with constant boiling hydrochloric acid in a continuous extractor for about 18 hours. The pellets were then washed with deionized water until an acidic reaction could no longer be detected and then air dried on a steam bath to constant weight. One hundred grams of the resulting dried pellets were treated with a solution of 10 grams of potassium dihydrogen phosphate in 190 ml. of water. The pellets were soaked in this solution for ½ hour, filtered to remove excess liquor and dried to constant weight in a vacuum oven at 70°C. The resulting dried pellets contained about 3.2% potassium dihydrogen phosphate.

A short 1⅛ inch I.D. stainless steel tube was fitted with a gas and a liquid inlet tube. The end of the gas inlet tube was restricted so as to provide a 6–12 p.s.i.g. back pressure under normal operating conditions. Both tubes were juxtaposed so as to cause any liquid fed to the system to aspirate as a uniform fine mist. A third inlet tube was placed above the first two so that additional gas could be provided to the chamber in a relatively non-turbulent manner thus helping to sweep the mist from the liquid feed smoothly through the system.

The tubular reactor was filled with above potassium dihydrogen phosphate catalyst so as to provide a bed 6 inches long. The top of this bed was positioned within ¼ to ½ inch of the liquid feed tube. Close proximity of the catalyst bed to the feed tube minimizes the time during which the finely divided liquid stream is in free flight without being in contact with the catalyst. Minimizing free flight time was found to be important since undesirable residue forming side-reactions can become a significant factor in the total process in the absence of contact with the catalyst bed.

Referring to the apparatus above-described, a 72% w/w aqueous solution of citramalic acid was metered to the inlet system at a rate of 1.6 ml./minute (1.9 gm./minute). Nitrogen gas preheated to 435°C. was fed to the aspirator inlet at such a rate as to result in 10 lbs./inch$^2$ back pressure. The nitrogen flow rate, observed using a rotometer calibrated at room temperature, was found to be 5.4 liters/minute. A relatively small amount of nitrogen sweep gas was also admitted to the system. The temperature of the catalyst bed was held between 235°–280°C. by adjustments of external heat supplied by electrical resistance heaters.

Exactly at what point in this process the relatively non-volatile acid feed mist becomes transformed to a vapor has not been determined. The catalyst bed, however, did not become wet at any time in the reaction. The superficial contact time of the vapors in the catalyst bed as calculated by volume displacemnt was about 0.25 seconds.

The addition was continued until the entire system reached a steady state. Then a series of traps as described previously was connected to the outlet of the reactor and the product was collected for about 25 minutes. The amount of citramalic acid solution added during this time was 38 ml., equivalent to 36 grams of pure, dry citramalic acid.

At the end of the run the contents of the traps were transferred to a common receptacle using acetone washes. The resulting water white solution was heated briefly to transform any anhydride to free acid, and then concentrated at about 40°C. under reduced pressure. The concentrate was examined using thin layer chromatography, and showed only one spot which corresponded to the control sample of sample of authentic citraconic acid. The developing system employed consisted of the bottom layer of a mixture of chloroform, acetic acid, formic acid and water in a volume ratio of 25:5:1:1. Analyzed by vapor phase chromatography, the concentrate contained 24.4 grams of citraconic acid, representing a 77.5% stoichiometric yield. Proof of structure of the product was provided by azeotropic drying of the product and distillation of the resulting anhydride. The distilled product proved identical in all respects to an authentic specimen of citraconic anhydride.

EXAMPLE II

The method of Example I was repeated except that the addition rate of citramalic acid solution was reduced to 0.34 ml/minute and the catalyst maintained at a temperature of 320°–355°C. with 0.1 second contact time. The resulting product solution exhibited pale amber color and contained some methacrylic acid in addition to the desired citraconic acid. The yield of citraconic acid was 39%.

Decreasing contact time to 0.01 second and temperatue range to 320°–330°C. improved both yield and purity of the citraconic acid formed.

EXAMPLE III

The method of Example I was repeated except that a 5% w/v aqueous solution of mesaconic acid was substituted for the citramalic acid solution, the rate of addition of the solution being 0.88 ml/minute and the catalyst bed maintained at a temperature between 220° and 255°C. The product solution was water white and contained citraconic acid as the only substance detectable by thin layer chromatography. The stoichiometric yield of citraconic acid was 98%.

EXAMPLE IV

The method of Example I may be repeated with comparable results replacing citramalic acid with 3-methylmalic acid, and using a supported catalyst consisting of 20 wt. % calcium phosphate deposited on the Alundum support.

EXAMPLE V

A microreactor consisting of a stainless steel injection port insert of a vapor fractometer was filled to give a ½ inch long bed of a 20–60 mesh fraction of crushed Alundum heat exchanger pellets (Norton BA 307). The injector port was heated to 335°C. and while nitrogen carrier gas was fed at 5 ml/minute, a solution of 0.4 g. of paraconic acid in 0.4 ml of water was charged at the rate of about 0.4 μl/minute. The temperature was slowly raised to 358°–377°C. A yield of 68% citraconic anhydride was obtained.

EXAMPLE VI

The acid washed Alundum support of Example I was crushed and screeened to give a 40–60 mesh fraction which was treated with an aqueous solution of potassium dihydrogen phosphate so as to provide a 5% addition of the phosphate salt after drying. The procedure of Example V was repeated at an operating temperature of 330°–340°C. A yield of 96% citraconic anhydride was obtained.

EXAMPLE VII

The method of Example I may be repeated with comparable results, replacing potassium dihydrogen phosphate with lithium dihydrogen phosphate, sodium dihydrogen phosphate, potassium pyrophosphate, sodium pyrophosphate, calcium pyrophosphate, rubidium phosphate, cesium dihydrogen phosphate, calcium phosphate, sodium phosphate, barium phosphate, lithium phosphate, potassium metaphosphate, sodium tripolyphosphate and magnesium phosphate.

EXAMPLE VIII

The method of Example I may be repeated with comparable results, replacing the Alundum support with the following materials made by the Norton Company:
SiC — tradename is Crystolon
$Zr(SiO_2)_2$ — tradename is Zircon
$ZrO_2$ — tradename is Zirconia
70 wt. percent $Al_2O_3$ and 29 wt. percent $SiO_2$ — tradename is Mullite.

EXAMPLE IX

The method of Example III was repeated replacing the mesaconic acid solution with an aqueous solution containing 1% w/w each of citramalic, paraconic and mesaconic acids. A water white solution containing citraconic acid in 86% stoichiometric yield was obtained.

EXAMPLE X

The method of Example III was repeated with an aqueous solution containing 5% w/w each of citramalic, paraconic and mesaconic acids. Citraconic acid was obtained in 87% yield.

EXAMPLE XI

The method of Example I may be repeated with a catalyst consisting of 0.01% by weight of potassium dihydrogen phosphate based on total weight of catalyst and support, maintaining a temperature of 220°–280°C. and a gas flow adjusted to provide a 5 second contact time. Comparable results are obtained.

EXAMPLE XII

Into a short path micro-distilling apparatus was placed 0.58 grams of crystalline citramalic acid. The distillation flask was immersed in an oil bath maintained at 220°–235°C. The distilled product was collected over a 15 minute period. Vapor phase chromatographic assay disclosed 0.23 grams of citraconic acid as its anhydride representing a 53% stoichiometric yield. Thin layer chromatography disclosed a small amount of citramalic acid and a trace of itaconic acid accompanying the major citraconic product. About 5% by weight of the original charge remained undistilled in the distillation flask.

EXAMPLE XIII

A 15 ml distillation flask fitted with a Claisen distillation head, addition funnel, thermometer, condenser and a series of ice and dry ice cooled receivers was heated in an oil bath maintained at 192°–5°C. A solution of 10 grams of citramalic acid and 0.16 grams of potassium dihydrogen phosphate in 5.4 ml of water was placed in the addition funnel. The apparatus was evacuated and the contents of the addition funnel plus a small additional quantity of water to rinse the funnel were dropped into the distillation flask over a period of an hour. During this time the internal temperature varied between 160° and 175°C. The distillate collected in the receivers was analyzed by vapor phase chromatography. The yeild of citraconic acid as its anhydride was 76%.

EXAMPLE XIV

The method of Example XII was repeated except that 0.77 grams of crystalline paraconic acid was used in place of citramalic acid, and the oil bath temperature was maintained at 280°–290°C. The distilled product was collected over a 15 minute period. By vapor phase chromatographic assay, the distillate was shown to contain 0.53 grams of citraconic acid as the anhydride, a 79% stoichiometric yield. A small amount of paraconic acid was detected in the citraconic anhydride by thin layer chomatography.

EXAMPLE XV

The importance of a suitable catalyst in the thermolytic conversion of mesaconic acid to citraconic acid is exemplified in the following experiments:

An 8 × 175 mm glass tube was rinsed with strong aqueous hydrochloric acid, then with deionized water and dried. About 0.2 grams of mesaconic acid was placed in the test tube and the tube immersed about ¾ of its length in a 200°C. stirred oil bath. The oil bath was heated until all the mesaconic acid acid was melted (oil bath temperature between 215° and 223°C.). The test tube was then allowed to cool and its contents dissolved in 0.5 ml of deuterated dimethylsulfoxide containing tetramethylsilane internal standard. NMR data showed absorption at 6.57 ppm (vinyl protons of mesaconic acid) and 2.18 ppm (methyl protons of mesaconic acid). No absorption could be detected at 6.93 or 6.62 ppm (vinyl protons of citraconic anhydride or acid, respectively) or at 2.14 ppm (methyl protons of citraconic anhydride or acid). The limits of detection are under 0.5%.

When the experiment was repeated at an oil bath temperature of 250°C. for 3 minutes, about 8% citraconic formation was observed via NMR absorption. A duplicate experiment in which 0.004 grams of potassium dihydrogen phosphate was mixed with the mesaconic acid before heating resulted in increasing the citraconic yield to 15%.

Repetition of the method of Example XII using 0.01 grams of potassium dihydrogen phosphate as the catalyst gave a citraconic yield of 70%. A similar experiment using 0.1 grams of sodium phosphate as the catalyst gave a citraconic yield of 72%. Similar results are obtained when 0.01 wt. % of potassium dihydrogen phosphate, based on citramalic acid, is used for catalysis.

Further comparison can be made from the results in Examples VII and VIII.

EXAMPLE XVI

The experiments of Example XV were repeated with comparable results, replacing mesaconic acid with paraconic acid.

EXAMPLE XVII

The influence of temperature on the thermolytic conversion of mesaconic acid to citraconic acid and the effect of catalysis in lowering effective temperatures are exemplified as follows:

A solution of 1.9 grams of mesaconic acid and 0.9 grams of cyclohexanone diluted to 10 ml with methyleneglycol monomethyl ether was charged at 0.46 µl/minute to a microreactor consisting of a stainless steel injection port insert of a vapor fractometer. While nitrogen carrier gas was fed at 5 ml per minute, the temperature was slowly raised from 335° to 490°C. The average yield of citraconic anhydride was observed to increase from 13% at 335°–400°C. to 30% at 400°–450°C to 59% at 450°–490°C.

These results are in contrast to the catalysis reactions of Example III where a 98% yield was obtained at a temperature range of 220°–255°C. and Example VI with a 96% yield at 330°–340°C.

What is claimed is:

1. A process for the preparation of citraconic anhydride or acid which comprises heating in an inert atmosphere at a temperature of 220°–280°C at a contact time of 0.2 – 1 second and under a pressure of 15–100mm of mercury a five-carbon acid selected from the group consisting of citramalic acid, mesaconic acid, paraconic acid, 3-methylmalic acid, or mixtures thereof, in the presence of a catalyst selected from the group consisting of an alkali or alkaline earth metal salt of a phosphoric acid selected from the group consisting of potassium pyrophosphate, sodium pyrophosphate, calcium pyrophosphate, strontium pyrophosphate, rubidium phosphate, cesium phosphate, barium phosphate, calcium phosphate, sodium tripolyphosphate and potassium metaphosphate, removing formed gaseous product from the reaction zone and recovering said product as citraconic acid or anhydride.

2. A process for the preparation of citraconic anhydride or acid which comprises:
   a. continuously introducing a five-carbon acid selected from the group consisting of citramalic acid, mesaconic acid, paraconic acid, 3-methylmalic acid, or mixtures thereof, in the presence of an inert carrier gas into a reaction bed composed of a support material containing deposited thereon a catalyst selected from the group consisting of an alkali or alkaline earth metal salt of a phosphoric acid selected from the group consisting of potassium pyrophosphate, sodium pyrophosphate, calcium pyrophosphate, strontium pyrophosphate, rubidium phosphate, cesium phosphate, barium phosphate, calcium phosphate, sodium tripolyphosphate and potassium metaphosphate;
   b. contacting said five-carbon acid, or mixtures thereof, with said reaction bed at a temperature of 220°–280°C at a contact time of 0.2 – 1 second and under a pressure of 15–100mm of mercury;
   c. removing from the reactor bed the fomed gaseous product; and
   d. recovering said product as citraconic anhydride or acid.

3. The process of claim 1 wherein said catalyst is sodium or potassium dihydrogen phosphate.

4. The process of claim 2 whrein said catalyst is sodium or potassium dihydrogen phosphate.

5. The process of claim 1 wherein said five-carbon acid is citramalic acid.

6. The process of claim 1 wherein said five-carbon acid is mesaconic acid.

7. The process of claim 1 wherein said five-carbon acid is paraconic acid.

8. The process of claim 2 wherein said five-carbon acid is citramalic acid.

9. The process of claim 2 wherein said five-carbon acid is mesaconic acid.

10. The process of claim 2 wherein said five-carbon acid is paraconic acid.

* * * * *